United States Patent [19]
Baer

[11] Patent Number: 5,840,492
[45] Date of Patent: Nov. 24, 1998

[54] METHOD AND COMPOSITIONS FOR DETECTING HEMATOPOIETIC TUMORS

[75] Inventor: Richard J. Baer, Dallas, Tex.

[73] Assignee: University of Texas System Board of Regents, Austin, Tex.

[21] Appl. No.: 558,340

[22] Filed: Nov. 15, 1995

Related U.S. Application Data

[63] Continuation of Ser. No. 371,676, Jan. 12, 1995, abandoned, which is a continuation of Ser. No. 152,973, Nov. 15, 1993, abandoned, which is a continuation of Ser. No. 33,060, Mar. 10, 1993, abandoned, which is a continuation of Ser. No. 763,377, Sep. 20, 1991, abandoned, which is a continuation-in-part of Ser. No. 621,140, Nov. 28, 1990, abandoned, which is a continuation-in-part of Ser. No. 613,197, Nov. 14, 1990, abandoned, which is a continuation-in-part of Ser. No. 590,408, Sep. 28, 1990, abandoned.

[51] Int. Cl.$^6$ ....................................................... C12Q 1/68
[52] U.S. Cl. ............................................. 435/6; 536/24.31
[58] Field of Search .................................. 435/6; 536/24, 536/31

[56] References Cited

PUBLICATIONS

Hopman et al, Histochemistry, 85 (1986):1–4.
Chen et al, Enbo J, v. 9, 1990, pp. 415–424.
Suske et al, Nucleic Acidv Rev. v. 17, 1989, p. 4405.

*Primary Examiner*—James Ketter
*Attorney, Agent, or Firm*—Jenkens & Gilchrist, P.C.

[57] ABSTRACT

Methods and compositions for the diagnosis and prognosis of hematopoietic tumors, such as T-cell acute lymphoblastic leukemia, in a human. The invention relates to using nucleic acid hybridization probes to detect, by fluorescent in situ chromosome hybridization, deletion of tal-1 locus on chromosome 1 from human cells to confirm T-cell acute lymphoblastic leukemia in the patient.

9 Claims, 10 Drawing Sheets

BamH1
GGATCCCTTGATCCTGGAGCCGGTGGCCCGCAGTTCTCCAAGAAGACTTGGGATTGGTGTGAGCGCGGGAACCAGTGCGGGGCGCTGATTGGTCGGCAC 100

ACCAATACGTAACGGGCGACCGTGCGCGGCTCTCTAGCACACCCCCGCTCCCTGACTGGCGAGGTTTCTGACCAGTCAGCAGGCGTGGCGCGCCTTCAG 200

TTTCGCGAGCTTGTGTTTGCCGCCTCAGTTCCCGCGACCCCAAGCGTCCCAGAGAGGGGCCGGCGGGTGGCGCTCCTTGGAGCCGGCTCCCGCTC 300

CTACCCTGCAAACAGACCTCAGCTCCGGGAAGTTGCGGTAAGTGGAGCTTTGTGCTCCTGGTTCCCCTGAGAGGGGCAGCGGGGCCCTGGGAAGGT 400

TGGTGGGTAACATTCAAAGCCCTGTAGTGGGTTCCGCCCCTCCAGGAGCCTGGAGCAGATGACGAGAAGGGGAGCTACTGGGAGAAATTAAGCAGTCCATG 500
                                                                                    oligonucleotide C AAATCCTTGGGTATCATCTGAGCTAAGGTATGTGAAAGAGGTTTTGCAGTCGATAACGTGCCATTTAAAGTTGTTTTACGGTGGAATTTCTTGAGGACT 600

GAAACCTTGAATGCTCGCTCTTGCATTCCTCACAATTTcggatcaaaTCATTTCTTCTTCGTGGTTGTGTGTGCATGCGGTGGGATTGTGAGAGAGTGCGTTC 700
                                     rearrangement                  oligonucleotide D
                                         site

FIG. 7

A  germline AA-0.6
GAAACCTTGAATGCTCGCTCTTGCATTCCTCACAATTTCTGGCTCACACTCTGCTACGTAGTAGTAAGGGATCAGTTAATGTTTGAAGTTC
                                           ********

B  tal^d junction
GAAACCTTGAATGCTCGCTCTTGCATTCCTCACAATTTCcggatcaaaTCATTTCTTCGTGGTTGTGTGCATGCGGTGGGATTGT
                                                                    Sph1

C  germline B2EE-2.0
CCTTTTCCTTACGCAATATACAGAAATGCGGCGAGGCTGTGGTTTTCATTTCTTCTTCTTCGTGGTTGTGTGCATCGGTGGGATTGT
                      ********                                      Sph1

FIG. 8

```
                                                         *******
germline(AA-0.6)    CATTCCTCACAATTTCTGGCTCACACTCTGCTACGTAGTAAGGG
                                                         ←
RPMI 8402           CATTCCTCACAATTTC          cggatcaaa          TCATTTCTTTC
CCRF-HSB-2          CATTCCTCACAATTTCTGGCTCA   tct               GTTGGTTTTCATTTCTTTC
MOLT 16             CATTCCTCACAATTTCTGGCTCA   ttaggggttc        GGTTTTTCATTTCTTTC
CCRF-CEM            CATTCCTCACAATTTCTGGC      aagtgga           TTGGTTTTCATTTCTTTC
PATIENT  B          CATTCCTCACAATTTCTGGCT     gg                GGTTTTCATTTCTTTC
         C          CATTCCTCACAATTTCTGG       gaaacgactt        TTGGTTTTCATTTCTTTC
         E          CATTCCTCACAATTTCTGG       g                 GGTTTTCATTTCTTTC
         G          CATTCCTCACAATTTCTGGC                        GTTGGTTTTCATTTCTTTC
         I          CATTCCTCACAATTTCTGGCTC                      TTTCATTTCTTTC
         53         CATTCCTCACAATTTCTGG       gaatcggg          GGTTTTTCATTTCTTTC
         56         CATTCCTCACAATTTCTGGC      tctggg            TGGTTTTCATTTCTTTC
         58         C                         tc                TGGTTTTTCATTTCTTTC
         60         CATTCCTCACAATTTCTGGCTCA   gcgccttcaacc      GTTGGTTTTCATTTCTTTC
         64         CATTCCTCACAATTTCTGGCTCA   taacaggactaaa     TGGTTTTCATTTCTTTC
         66         CATTCCTCACAATTTCTGGCTC    c                 TGGTTTTCATTTCTTTC
         68         CATTCCTCACAATTTCTGG       ccagga            GGTTGGTTTTCATTTCTTTC
         80         CATTCCTCACAATTTCTGGCTC    ttacagaga         GTTGGTTTTCATTTCTTTC
         82         CATTCCTCACAATTTCTGGCTCA   tttc              TGGTTTTCATTTCTTTC
         83         CATTCCTCACAATTTCTGGCTCA   ttggaag           TGGTTTTCATTTCTTTC
         91         CATTCCTCACAATTTCTGG       tagtttaagtgg      GTTGGTTTTCATTTCTTTC
         93         CATTCCTCACAATTTCTGG       gtaggg            GGTTTTCATTTCTTTC
         99         CATTCCTCACAATTTCT         ccctctaagg        TGGTTTTCATTTCTTTC
                                                                                ←
germline(B2EE-2.0)  AAATGCGGAGGCTGTGGTTGGTTTTCATTTCTTTC
                                ******
```

FIG. 9

METHOD AND COMPOSITIONS FOR DETECTING HEMATOPOIETIC TUMORS

This is a continuation application of U.S. application Ser. No. 08/371,676, filed Jan. 12, 1995, now abandoned, an application which is a continuation application of U.S. application Ser. No. 08/152,973, filed Nov. 15, 1993, now abandoned, which is a continuation application of U.S. application Ser. No. 08/033,060, filed Mar. 10, 1993, now abandoned, which is a continuation application of U.S. application Ser. No. 07/763,377, filed Sep. 20, 1991, now abandoned, which is a continuation-in-part application of U.S. application Ser. No. 07/621,140, filed Nov. 28, 1990, now abandoned, which is a continuation-in-part application of U.S. application Ser. No. 07/613,197, filed Nov. 14, 1990, now abandoned, which is a continuation-in-part application of U.S. application Ser. No. 07/590,408, filed Sep. 28, 1990, now abandoned.

FIELD OF THE INVENTION

The present invention relates to methods and compositions for diagnosis and prognosis of hematopoietic tumors in a human, and in particular, relates to methods and compositions for detecting alteration of tal-1 locus on chromosome 1 of human cells for the diagnosis and prognosis of T-cell acute lymphoblastic leukemia.

BACKGROUND OF THE INVENTION

Certain tumors are characterized by unique chromosome abnormalities or alterations that are present in a significant proportion of affected patients (Yunis, J. J. (1983) Science 221, 227–236). Much evidence supports the view that these abnormalities represent genetic events that promote development of the associated neoplasm (Mitelman, F. (1987) Cancer Cytogenetics (New York: A. R. Liss)). For example, the t(8;14)(q24;q32) translocation is observed in the malignant cells of nearly 90% of patients with Burkitt's lymphoma; at the molecular level, this defect represents the activation of the c-myc proto-oncogene by transposition from its normal location on chromosome 8 into the immunoglobulin heavy chain locus on chromosome 14 (Leder, P. et al. (1983) Science 222, 765–771; Rabbitts T. H. (1985) Trends in Genetics 1, 327–331).

By contrast, cytogenetic studies have not uncovered a major karyotypic abnormality or alterations associated with T cell acute lymphoblastic leukemia (T-ALL). Instead, a number of minor defects have been reported, many of which feature cytogenetic breakage within the T cell receptor (TCR) genes on chromosomes 7 and 14 (Boehm, T. and Rabbitts, T. H. (1989) FASEB J. 3, 2344–2359; Tycko, B. and Sklar, J. (1990) Cancer Cells 2, 1–8). Individually, these chromosome abnormalities are present in relatively small proportions of T-ALLs; for example, the most prevalent, the t(11;14)(p13;q11) translocation, is only observed in about 7% of T-ALL patients. Nevertheless, each has been implicated as a contributing factor in leukemogenesis on the basis of its recurrence in unrelated patients and its unique association with T-ALL.

Chromosome 1 harbors a genetic locus (designated tal, for T-cell acute leukemia) involved in leukemogenesis. The tal-1 gene was identified upon analysis of t(1;14)(p32;q11), a chromosome translocation observed in only 3% of T-ALL patients (Chen, Q. et al. (1990) EMBO J. 9, 415–424; Brown, L. et al. (1990) EMBO J. 10, 3343–3351; Bernard, O. et al. (1990) Genes, Chromosomes and Cancer 1, 194–208; Begley, C. G. et al. (1989) Proc. Natl. Acad. Sci. USA 86, 10128–10132; Finger, L. R. et al. (1989) Proc. Natl. Acad. Sci. USA 86, 5039–5043). As a consequence of the translocation, tal-1 is transposed from its normal location on chromosome 1 into the T cell receptor α/δ chain locus on chromosome 14. The amino acid translation of tal-1 includes sequences homologous to the helix-loop-helix (HLH) motif (Chen, Q. et al. (1990) EMBO J. 9, 415–424; Begley, C. G. et al. (1989) Proc. Natl. Acad. Sci. USA 86, 10128–10132), a DNA-binding domain present in a family of proteins involved in the control of cell growth and differentiation (Villares, R. and Cabrera, C. V. (1987) Cell 50, 415–424; Murre, C. et al. (1989) Cell 56, 777–783). The homology domains of several HLH proteins have been shown to specifically bind core sequences of transcription enhancer elements, including those associated with the immunoglobulin kappa chain locus and the muscle creatine kinase gene (Murre, C. et al. (1989) Cell 56, 777–783; Murre, C. et al. (1989) Cell 58, 537–544; Lassar, A. B. et al., (1989) Cell 58, 823–831; Henthorn, P. et al., (1990) Science 247, 467–470). Thus, proteins of the HLH family may serve as transcriptional regulatory factors, a function that accords well with their profound influence over both normal and malignant development.

Several genes that encode HLH proteins have been implicated in human leukemia, including the c-myc lyl-1, and E2A proto-oncogenes (Mellentin, J. D. et al. (1989) Cell 58, 77–83; Mellentin, J. D. et al. (1989) Science 246, 379–382; Nourse, J. et al. (1990) Cell 60, 535–545; Kamps, M. P. et al. (1990) Cell 60, 547–555). Therefore, it is tempting to propose that the t(1;14)(p32;q11) translocations alter tal-1 gene expression in a manner that promotes T-ALL formation. However, t(1;14)(p32;q11) is a rare marker of T-ALL, detectable in only 3% of patients with the disease.

For diagnostic and prognostic purposes, therefore, it is desirable to have a more common marker of T-ALL.

SUMMARY OF THE INVENTION

Accordingly, an object of the present invention is to provide a novel method for the diagnosis and prognosis of hematopoietic tumors in a human patient.

Another object of the present invention is to provide a novel method for the diagnosis and prognosis of hematopoietic tumors in a human patient by detecting an alteration of tal-1 locus on chromosome 1 in cells of a human patient.

Still another object of the present invention is to provide a novel method for the diagnosis of T-cell acute lymphoblastic leukemia in a human patient by detecting the rearrangement in chromosome 1 at a locus of tal-1.

Yet another object of the present invention is to provide a nucleic acid hybridization probe for the detection of altered tal-1 locus on chromosome 1 in cells of a human patient.

Still another object of the present invention is to detect deletion of the tal-1 gene in human cells by fluorescent in situ chromosome hybridization.

Additional objects, advantages and novel features of the invention will be set forth in part in the description which follows, and in part will become apparent to those skilled in the art of examination of the following, or may be learned by the practice of the invention.

BRIEF DESCRIPTION OF THE DRAWINGS

FIG. 7 shows nucleotide sequence encompassing the tal$^d$ rearrangement of RPMI 8402.

FIG. 8 illustrates the deletion junction of tal$^d$ from RPMI8402 cells.

FIG. 9 shows that tal$^d$ deletion junctions resemble the coding joints of assembled immunoglobulin genes.

DETAILED DESCRIPTION OF THE INVENTION

Figure 1A:
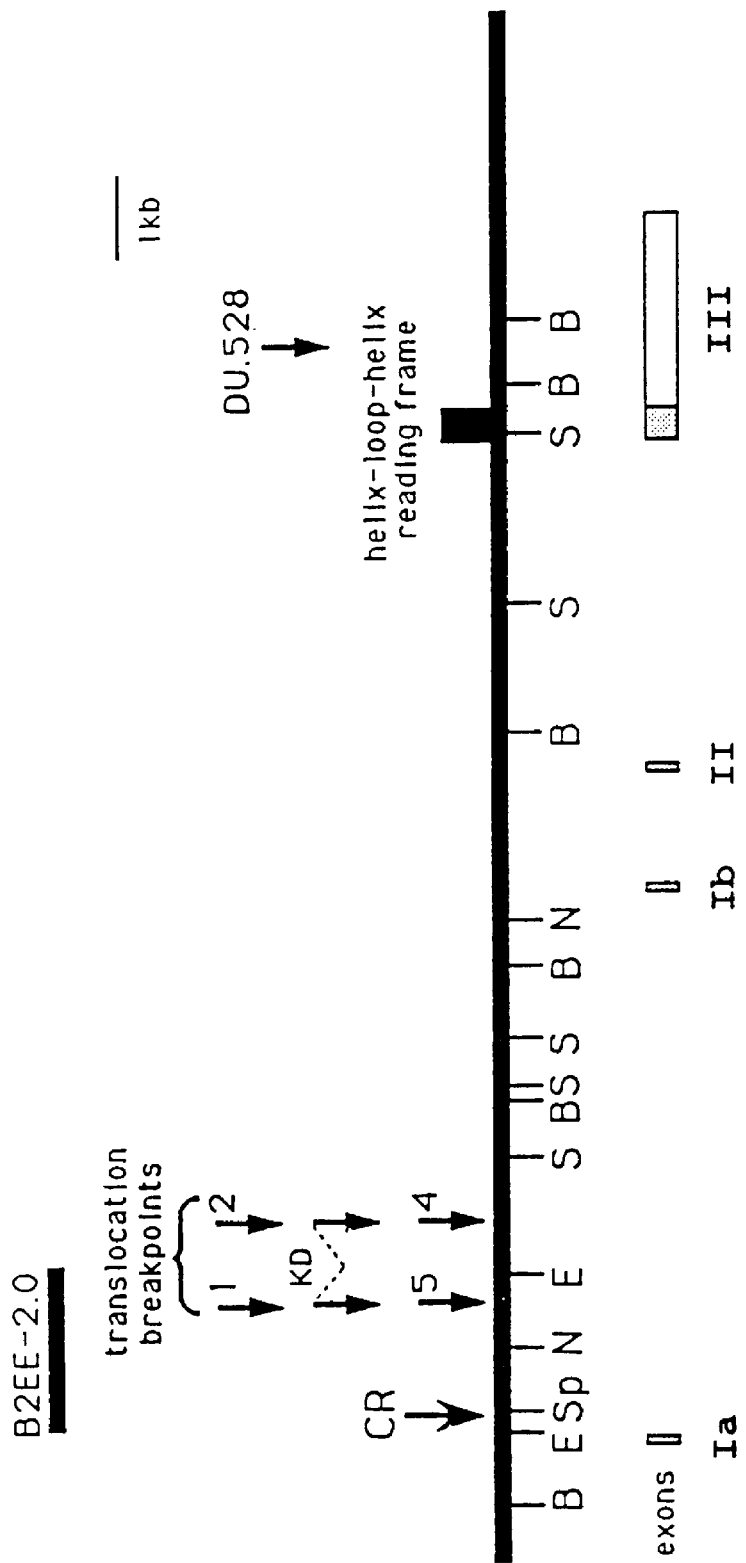
FIGS. 1A–1C illustrates rearrangement of the tal-1 gene in T-ALL cells.

In accordance with the subject invention, novel methods and compositions are provided for the diagnosis and prognosis of hematopoietic tumors in a human host suspected of having such tumors. It has now been demonstrated in the present invention that a locus (designated tal) on chromosome 1 is altered in the tumor cells of a significant proportion (about 25%) of patients with T cell acute lymphoblastic leukemia (T-ALL). The tal-1 locus alterations on chromosome 1 can be readily detected by Southern hybridization analysis or by the polymerase chain reaction. The uses of this invention are threefold: First, the tal-1 locus alterations on chromosome 1 can be used to facilitate the diagnosis of T-ALL. Second, the tal-1 locus alterations on chromosome 1 can be used prognostically to identify T-ALL patients that are likely to suffer a relapse of leukemia after the initial therapy. Third, the tal-1 locus alterations on chromosome 1 can also be used prognostically to track minimal levels of residual disease in T-ALL patients during treatment and during remission.

Surprisingly, the rearrangements of tal-1 locus on chromosome 1 observed in different patients are identical—i.e., they all arose from a precise 90 kilobasepair ("kb") deletion that disrupts the coding region of tal-1 in a manner analogous to the t(1;14)(p32;q11) translocation. The extraordinary precision of these deletions (designated tal$^d$) suggests that they are mediated by a site-specific DNA recombinase. Moreover, analysis of the deletion junctions indicates that tal$^d$ rearrangement is engendered by aberrant activity of the same recombinase that controls immunoglobulin and T cell receptor gene assembly.

The term "tal-1 locus" as used herein denotes a region of DNA approximately 200 kb upstream and approximately 200 kb downstream of tal-1 transcription unit. The DNA extract containing chromosome 1 can be isolated from a human tissue such as blood or bone marrow.

The structural defects that activate proto-oncogenes are of various types, including point mutation, retroviral insertion, gene amplification and chromosome translocation (Klein, G. and Klein, E. (1985) Nature 315, 190– 195). The tal-1 gene was originally implicated in oncogenesis in studies of t(1;14)(p32;q11), a chromosome translocation uniquely associated with T cell acute lymphoblastic leukemia (T-ALL) (Chen, Q. et al. (1990) EMBO J. 9, 415–424; Bernard, O. et al. (1990) Genes, Chromosomes and Cancer 1, 194–208; Begley, C. G. et al. (1989) Proc. Natl. Acad. Sci. USA 86, 10128–10132; Finger, L. R. et al. (1989) Proc. Natl. Acad. Sci. USA 86, 5039–5043). As a consequence of the translocation, tal-1 is transposed from its normal position on chromosome 1 into the T cell receptor α/δ chain locus on chromosome 14, whereupon its expression is presumably altered in a manner that promotes leukemogenesis. However, since t(1;14)(p32;q11) is observed in only 3% of T-ALL patients, malignant activation of tal-1 by chromosome translocation is clearly an uncommon pathway toward the formation of T-ALL. It has been found in the present invention that about 25% of T-ALL patients harbor a tumor-specific deletion of approximately 90 kilobasepairs from one allele of the tal-1 locus. Since the deletion (designated tal$^d$) is found in tumors without detectable cytogenetic lesions of chromosome 1, it is apparently beyond the current resolution of karyotype analysis.

Structural deletions of the rb-1 locus are routinely observed in the malignant tissues of patients with retinoblastoma (Dryja, T. P. et al. (1986) Proc. Natl. Acad. Sci. USA 83, 7391–7394). Nevertheless, these deletions are of variable length and probably serve to inactivate expression of rb-1, a gene that promotes malignancy in a recessive fashion by loss of genetic function. In contrast, the tal$^d$ deletions exhibit nearly identical endpoints in different T-ALL patients. Hence, tal$^d$ rearrangement is a distinct mechanism of oncogene alteration in which a common genetic lesion is generated independently in different patients by site-specific DNA recombination.

The tal$^d$ rearrangement was observed in at least 25% of T-ALL samples, including leukemic specimens obtained directly from T-ALL patients and leukemic cell lines established from these patients. No similar lesions in other hematopoietic tumors, including pre-B-ALL and the other forms of T cell neoplasia, were observed. It has been shown that tal-1 is altered by t(1;14)(p32;q11) translocation in DU.528 (Begley, C. G. et al. (1989) Proc. Natl. Acad. Sci. USA 86, 10128–10132; Finger, L. R. et al. (1989) Proc. Natl. Acad. Sci. USA 86, 5039–5043), a cell line derived from a rare stem cell leukemia (Kurtzberg, J. et al. (1985) J. Exp. Med. 162, 1561–1578). It may be significant, however, that the DU.528 patient presented with T-ALL at the initial diagnosis (Hershfield, M. S. et al. (1984) Proc. Natl. Acad. Sci. USA 81, 253–257). Thus, alteration of the tal-1 gene, either by tal$^d$ rearrangement or t(1;14)(p13;q11) translocation, appears to be predominantly, if not exclusively, associated with T-ALL.

Although the initiation sites of tal-1 gene transcription are presently unknown, two distinct mRNA species have been identified, both of which encode the HLH domain (Chen Q. et al. (1990) EMBO J. 9, 415–424; Begley, C. G. et al. (1989) Proc. Natl. Acad. Sci. USA 86, 10128–10132). These are clearly generated by alternative RNA splicing; hence, type A mRNA includes the three coding exons provisionally designated Ia, II and III, while type B mRNA includes exons Ib, II and III (see FIG. 1A discussed below). Three of the four t(1;14)(p32;q11) translocations analyzed feature breakage within a 1 kb region of the tal-1 locus. It is noteworthy that the translocation breakpoint region and the site of tal$^d$ rearrangement both fall between exons Ia and Ib. Thus, tal$^d$ deletion and t(1;14)(p32;q11) translocation are structurally equivalent alterations of tal-1 in that each removes exon Ia from the remainder of the locus and thereby precludes the production of type A mRNA. The effect of these lesions on expression of type B mRNA cannot be evaluated until its transcription start site is defined. Nevertheless, the truncation of tal-1 observed in T-ALL resembles the structural alterations sustained by genes that encode other HLH proteins implicated in human leukemogenesis. For example, it has been proposed that the malignant potential of c-myc and lyl-1 can also be unleashed by chromosome translocations that remove or mutate the 5' coding exons of these genes (Rabbitts, T. H. et al. (1984) Nature 309, 592–597; Taub, R. et al. (1984) Cell 36, 339–348; Pelicci, P.-G. et al. (1986) Proc. Natl. Acad. Sci. USA 83, 2984–2988; Hann, S. R. et al. (1988) Cell 52, 185–195; Mellentin, J. D. et al. (1989) Cell 58, 77–83).

A remarkable feature of the tal$^d$ rearrangement is its apparent site-specificity, especially in view of the substantial size of the deletion that it engenders. The only site-specific DNA rearrangements observed in vertebrates are those involved in the assembly of the immunoglobulin (Ig) and T cell receptor (TCR) genes during lymphoid development (Tonegawa, S. (1983) Nature 302, 575–581; Blackwell, T. K. and Alt, F. W. (1989) J. Biol. Chem. 264, 10327–10330; Lewis, S. and Gellert, M. (1989) Cell 59, 585–588). Since tal$^d$ rearrangements arise in T-lineage cells, these may also be mediated by the same recombination system. Rearrangements within the Ig/TCR loci are directed by signals that flank the rearranging gene segments and presumably serve as recognition sites for the Ig/TCR recombinase. These signals are comprised of a conserved heptamer element that is separated from a conserved nonamer by either 12 or 23 basepairs of relatively unconserved sequence. As illustrated in FIG. 9 discussed below, sequences bearing resemblance to the consensus heptamer of Ig/TCR recombination signals (CACAGTG) can be found at appropriate positions within germline DNA of both AA-0.6 (CACTCTG; marked by asterisks in FIG. 8 discussed later) and B2EE-2.0 (CACAGCC; marked by asterisks in reverse complement). These heptamers should be relatively inefficient at directing recombination since they are not associated with conserved nonamer elements and they bear sequence deviations from the consensus heptamer that are likely to reduce, but not eliminate, the rate of recombination (Hesse, J. E. et al. (1989) Genes & Development 3, 1053–1061).

The role of the Ig/TCR recombinase in tal$^d$ rearrangement can be further evaluated by examination of tal$^d$ deletion junctions from T-ALL patients. During normal Ig/TCR gene rearrangement, two reciprocal products of recombination are generated: a "coding joint," which constitutes the fusion of two gene segments of the rearranging locus, and a "signal joint," comprised of the two recombination signals that had previously flanked the rearranged gene segments. Signal joints are usually formed in a conservative fashion without the loss or gain of nucleotides at the recombination junction. In contrast, coding joints are diversified as a result of both the random trimming and random addition of nucleotides at the junction. Interestingly, the tal$^d$ deletion junctions bear a striking resemblance to the coding joints of assembled Ig/TCR genes. For example, if cleavage within germline AA-0.6 occurs adjacent to the proposed heptamer (see FIG. 9 discussed below), then a variable trimming of nucleotides (0 to 22 residues) clearly takes place before relegation of the AA-0.6 end to form tal$^d$; exonucleolytic trimming of the B2EE-2.0 sequence (0 to 8 residues) is also evident. Moreover, 21 of the 22 tal$^d$ junctions bear random nucleotides (0 to 13 residues) that are not derived from germline sequences, and thus may have been generated in a manner similar to the N-region nucleotides of Ig/TCR coding joints (Alt, F. W. and Baltimore, D. (1982) Proc. Natl. Acad. Sci. USA 79, 4118–4122). Some Ig/TCR coding joints acquire nonrandom insertions of defined mono- and di-nucleotides (designated P nucleotides) (Lafaille, J. J. et al. (1989) Cell 59, 859–870). Although the complete rules for their identification are complex, P nucleotides are only found appended to coding ends that have not suffered exonucleolytic trimming. Notably, a thymidine residue (underlined in FIG. 9 discussed below) that fulfills the criteria of P nucleotides can be seen in each of the six tal$^d$ junctions that bears an untrimmed AA-0.6 sequence (CCRF-HSB-2, MOLT16, and some patients).

The strong resemblance between tal$^d$ junctions and the coding joints of assembled Ig/TCR genes implies that tal$^d$ deletions are mediated by the Ig/TCR recombinase. Aberrant activity of the recombinase has also been implicated in the formation of chromosome translocations involving the Ig/TCR loci (Boehm, T. and Rabbitts, T. H. (1989) FASEB J. 3, 2344–2359; Tycko, B. and Sklar, J. (1990) Cancer Cells 2, 1–8). Nevertheless, at least one of the two recombining elements responsible for these translocations corresponds to an Ig/TCR sequence that normally serves as a recombination signal. In contrast, both recombining elements (i.e., the AA-0.6 and B2EE-2.0 heptamers) involved in tal$^d$ rearrangement are unnatural substrates for the recombinase; moreover, these are probably poor substrates as well, due to deviations from the consensus heptamer sequence and the absence of an associated nonamer element (Hesse, J. E. et al. (1989) Genes & Development 3, 1053–1061). In view of the likely inefficiency of tal$^d$ recombination, the recurrence of tal$^d$ in T-ALL patients is all the more remarkable and argues strongly that alteration of the tal-1 gene is a critical factor in T cell leukemogenesis.

The methods and compositions of the present invention utilize the following materials and general methods:

Tumor Specimens and Cell Lines

Leukemic specimens were provided by the Pediatric Oncology Group (St. Louis, Mo.); these represent peripheral blood or bone marrow aspirates obtained from T-ALL patients prior to treatment. Cell lines were either obtained from the American Type Culture Collection (Rockville, Md.) or they were kindly provided by Drs. Manuel Diaz (University of Chicago), Michael Krangel (Dana Farber Cancer Institute) or Peter Lipsky (U.T. Southwestern).

Molecular Studies

DNA extracted from patient specimens was analyzed by Southern hybridization with radiolabeled DNA probes (Southern, E. (1975) J. Mol. Biol. 98, 503–517; Feinberg, A. P. and Vogelstein, B. (1983) Anal. Biochem. 132, 6–13). Genomic DNA libraries of BamHI-digested patient DNAs were constructed in phage vector λ2001 (Karn, J. et al. (1984) Gene, 32, 217–224). A cDNA library of poly(A)-selected RNA from CCRF-CEM cells (Foley, G. E. et al. (1965) Cancer, 18, 522–529) prepared in the phage vector λZAP II (Short, J. M. et al. (1988) Nucleic Acids Res., 16, 7583–7600) was obtained from Clontech Laboratories, Inc. (Palo Alto, Calif.). These libraries were screened by the method of Benton and Davis (Benton, W. D. and David, R. W. (1977) Science, 196, 180–182), and restriction fragments of recombinant lambda phage DNA were subcloned into plasmid and M13 phage vectors (Yanisch-Perron, C. et al. (1985) Gene, 33, 103–119; Pridmore, R. D. (1987) Gene, 56, 309–312; Short, J. M. et al. (1988) Nucleic Acids Res., 16, 7583–7600). Nucleotide sequence analyses were performed on M13 single-stranded templates by the chain-terminator method (Sanger, F. et al. (1980) J. Mol. Biol., 143, 161–178).

Somatic Cell Hybrid Analyses

The B2EE-2.0 clone was used as a probe in Southern filter hybridizations with EcoRI-digested DNAs extracted from a panel of 17 human/hamster somatic cell hybrids with randomly segregated human chromosomes. The B2EE-2.0 probe hybridized with both human and hamster DNAs, but the resolvable difference in fragment size (human, 2.0 kb; hamster, 7.3 kb) allowed assessment of the presence or absence of human sequence among hybrids of the panel. The hybridization of B2EE-2.0 was perfectly concordant with chromosome 1 and randomly associated (18–65% discordancy) with every other human chromosome (Table 1). Many of the approximately 200 independent human-hamster hybrids generated and analyzed in the laboratory contain broken human chromosomes (Thompson, L. E. et al. (1987) Somat. Cell Mol. Genet., 13, 539–551). These were screened for hybrids in which chromosome 1 was disrupted as indicated by the presence of one or more human chromosome 1 markers in the absence of others. A panel of 29 such hybrids was identified and screened for the presence or absence of B2EE-2.0 in addition to five chromosome 1 markers representative of regions on the p and q arms— PGD at p36, AK2 at p34, PGM1 at p22, AT3 at q23, and PEPC at q24 or q42 (assignments from HGM9, Morton, N. E. and Bruns, G. A. (1987) Cytogenet. Cell Genet., 46, 102–130). The lowest levels of discordance were between B2EE-2.0 and the p-arm markers—24% with PGD, 24% with AK2, and 17% with PGM1. Discordancy between B2EE-2.0 and the q-arm markers was high (44% for AT3 and 75% for PEPC). The data indicate a chromosome 1 p location for B2EE-2.0.

TABLE 1

Concordancy analysis of each human chromosome with B2EE-2.0 in the 17 hybrids of the hybrid clone human mapping panel.

| Chrom | # of Hybrids[1] | | | | % | Chrom | # of Hybrids | | | | % |
|---|---|---|---|---|---|---|---|---|---|---|---|
| | +/+ | +/− | −/+ | −/− | Disc[2] | | +/+ | +/− | −/+ | −/− | Disc |
| 1 | 5 | 0 | 0 | 12 | 0 | 13 | 2 | 6 | 3 | 6 | 53 |
| 2 | 1 | 4 | 4 | 8 | 47 | 14 | 5 | 4 | 0 | 8 | 24 |
| 3 | 3 | 3 | 2 | 9 | 29 | 15 | 2 | 2 | 3 | 10 | 29 |
| 4 | 3 | 4 | 2 | 8 | 35 | 16 | 3 | 4 | 2 | 8 | 35 |
| 5 | 4 | 6 | 1 | 6 | 41 | 17 | 0 | 2 | 5 | 10 | 41 |
| 6 | 4 | 3 | 1 | 9 | 24 | 18 | 3 | 5 | 2 | 7 | 41 |
| 7 | 4 | 2 | 1 | 10 | 18 | 19 | 4 | 8 | 1 | 4 | 53 |
| 8 | 3 | 9 | 2 | 3 | 65 | 20 | 3 | 3 | 2 | 9 | 29 |
| 9 | 1 | 6 | 4 | 6 | 59 | 21 | 2 | 8 | 3 | 4 | 65 |
| 10 | 1 | 5 | 4 | 7 | 53 | 22 | 4 | 6 | 1 | 6 | 41 |
| 11 | 3 | 3 | 2 | 9 | 29 | X | 3 | 3 | 2 | 9 | 29 |
| 12 | 3 | 5 | 2 | 7 | 41 | | | | | | |

[1]+/+ have the chromosome and B2EE, +/− have the chromosome but not B2EE, −/+ do not have the chromosome but have B2EE, −/− have neither the chromosome nor B2EE.
[2]% discordant = # +/− and # −/+ divided by 17 × 100.

DNA Analysis and Cloning

DNA extracted from patient specimens and cell lines were analyzed by Southern hybridization with radiolabeled DNA probes (Southern, E. (1975) J. Mol. Biol. 98, 503–517; Feinberg, A. P. and Vogelstein, B. (1983) Anal. Biochem. 132, 6–13). Lambda phage libraries of genomic DNA from the SUP-T1 (Baer, R. et al. (1985) Cell 43, 705–713) and RPMI8402 cell lines (Baer, R. et al. (1988) EMBO J. 7, 1661–1668) were screened by the method of Benton and Davis (Benton, W. D. and Davis, R. W. (1977) Science 196, 180–1821977), and restriction fragments of recombinant phage DNA were subcloned into plasmid and M13 phage vectors (Yanisch-Perron, C. et al. (1985) Gene 33, 103–119; Pridmore, R. D. (1987) Gene 56, 309–312). Nucleotide sequence analyses were performed on M13 single-stranded templates by the chain-terminator method (Sanger, F. et al. (1980) J. Mol. Biol. 143, 161–178). Chromosomal localization of the AA-0.6 DNA fragment by somatic cell hybrid analysis was conducted exactly as described for the B2EE-2.0 fragment (Chen, Q. et al. (1990) EMBO J. 9, 415–424). Pulsed-field gel electrophoresis (Schwartz, D. C. and Cantor, C. R. (1984) Cell 37, 67–75) was conducted on a transverse alternating-field (Gardiner, K. et al. (1986) Som. Cell Mol. Genet. 12, 185–195) apparatus obtained from Beckman Instruments (GeneLine). DNA from tissue culture cells was prepared in agarose blocks for restriction endonuclease digestion (Smith, C. L. et al. (1988) In Davies, K (ed.), Genome Analysis: A Practical Approach. IRL Press, Oxford, pp. 41–47). Electrophoresis was carried out in TAFE buffer (10 mM Tris-acetate pH 7.0, 0.4 mM EDTA) at constant temperature (12° C.) and amperage (150 mA) using 10 second pulses for 20 hrs.

Polymerase Chain Reaction

Amplification of $tal^d$ deletion junctions was conducted by the polymerase chain reaction (Saiki, R. K. et al. (1988) Science, 239, 487–491) using oligonucleotide primers C (AGGGGAGCTCGTGGG AGAAATTAAG) and D (TCACAATCCCACCGCATGCACA). The reaction conditions were similar to those described (Cheng, J.-T. et al. (1990) J. Exp. Med. 171, 489–501). The amplification products were fractionated by electrophoresis on 10% polyacrylamide gels and visualized by ethidium bromide staining. After elution from the gel, the amplification products were phosphorylated with polynucleotide kinase (New England Biolabs) and cloned into the SmaI site of M13mp18 for nucleotide sequence analysis.

The following Example is given to further illustrate the present invention and is in no way intended to limit the scope of the present invention.

EXAMPLE

A. The tal-1 Gene is Altered in a High Proportion of T-ALL Patients

The tal-1 gene is comprised of multiple exons with amino acid coding potential. FIG. 1A shows a restriction map of the tal-1 gene in its normal configuration. The small arrows designate the sites of chromosome breakage due to t(1;14) (p32;q11) translocations from patients 4 and 5 (Chen, Q. et al. (1990) EMBO J. 9, 415–424), DU.528 (Begley, C. G. et al. (1989) Proc. Natl. Acad. Sci. USA 86, 10128–10132; Finger, L. R. et al. (1989) Proc. Natl. Acad. Sci. USA 86, 5039–5043), and Kd (Bernard, O. et al. (1990) Genes, Chromosomes and Cancer 1, 194–208); the translocation in patient Kd was accompanied by loss of sequences between the two arrows (Bernard, O. et al. (1990) Genes, Chromosomes and Cancer 1, 194–208). The large arrow indicates the downstream endpoint of the $tal^d$ deletion. The exons of tal-1 were localized by comparing sequences of tal-1 cDNA clones (Chen, Q. et al. (1990) EMBO J. 9, 415–424; Begley, C. G. et al. (1989) Proc. Natl. Acad. Sci. USA 86, 10128–10132) and a genomic DNA; the stippled regions of the tal-1 exons denote coding sequences and the open region denotes 3' non-coding sequence. Restriction sites are as follows: B, BamHI; E, EcoR1; N, NotI, S, SacI; Sp, SphI (SphI sites are not complete).

Two alternatively-spliced mRNA species have been identified by cDNA analysis, one of which includes exons Ia-II-III (type A) and the other exons Ib-II-III (type B). In three of four patients with t(1;14)(p32;q11) translocations, the chromosome 1 breakage occurred within a 1 kb region located just downstream of exon Ia (FIG. 1A). Thus, as a consequence of t(1;14)(p32;q11), the structure of tal-1 is often disrupted in a manner that precludes production of type A mRNA from the translocated allele.

The t(1;14)(p32;q11) chromosome translocation in leukemic cells is only observed in 3% of T-ALL patients. If this DNA rearrangement represents a junction of the t(1;14) (p32;q11) translocation, then sequences upstream of the divergence point should be derived from chromosome 1. Therefore a 2.0 kb EcoRI fragment from this region was isolated and subcloned into a plasmid vector. This clone (B2EE-2.0) was then used as a probe in Southern filter hybridizations with DNAs extracted from a panel of 17 human/hamster somatic cell hybrids with randomly segregated human chromosomes (Thompson, L. E. et al. (1987) Somat. Cell Mol. Genet., 13, 539–551; Stallings, R. L. et al. (1988) Am. J. Hum. Genet., 43, 144–151). The hybridization of B2EE-2.0 was perfectly concordant with chromosome 1 and randomly associated (18–65% discordancy) with every other human chromosome (Table 1). Furthermore, the pattern of hybridization with a panel of hybrids containing broken derivatives of chromosome 1 (Thompson, L. E. et al. (1987) Somat. Cell Mol. Genet., 13, 539–551) provided a regional localization of B2EE-2.0 to the short arm of chromosome 1. Thus the contiguity of sequences from chromosome 14 (i.e. TCR δ gene) and chromosome 1 (i.e. B2EE-2.0) in the 12.2 kb BamHI fragment of λB2 demonstrates that the intervening DNA rearrangement represents the junction of t(1;14)(p32;q11).

Because t(1;14)(p32;q11) is a rare marker of T-ALL, it was necessary to determine whether tal-1 is also altered in patients without obvious karyotypic abberations of chromosome 1. Therefore, leukemic DNAs derived from either established T-ALL cell lines or fresh T-ALL specimens were examined. FIG. 1 shows Southern analyses of BamHI-digested DNAs hybridized with B2EE-2.0, a probe representing sequences from the translocation breakpoint region of tal-1.

Figures 1B, 1C:
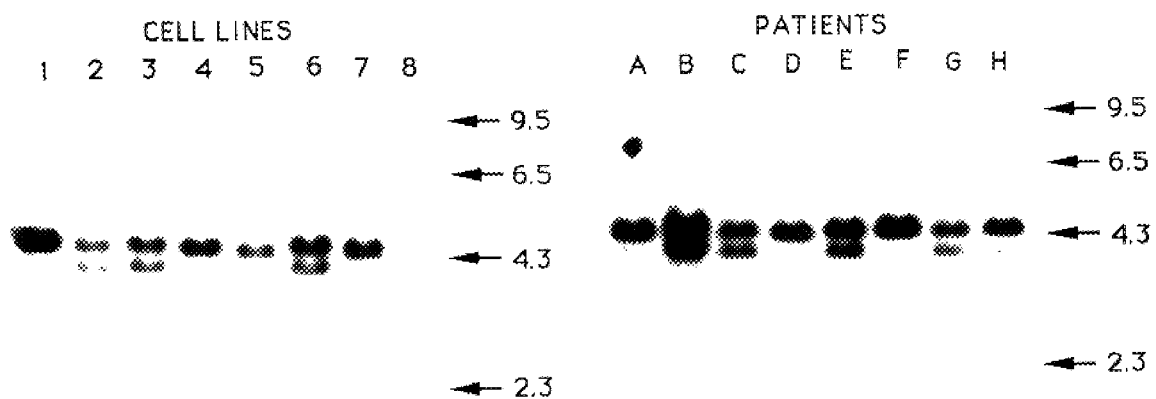

DNAs derived from eight T-ALL cell lines were examined and four of these displayed a rearranged 4.5 kb BamHI fragment in addition to the normal 5.0 kb fragment. FIG. 1B shows the rearrangement of the tal-1 gene in T-ALL cell lines. A Southern filter of BamHI-digested DNAs was hybridized with tal-1 probe B2EE-2.0. The DNAs were derived from T-ALL cell lines Jurkat (lane 1), RPMI8402 (2), CCRF-CEM (3), MOLT-3 (4), MOLT-13 (5), MOLT-16 (6), PEER (7), and CCRF-HSB-2 (8). The sizes of HindIII λDNA marker fragments are indicated in kb.

The tal-1 DNA rearrangement was also observed in fresh leukemic cells from four of eight T-ALL patients. FIG. 1C shows the rearrangement of the tal-1 gene in primary T-ALL cells. A Southern filter of BamHI-digested DNAs was hybridized with B2EE-2.0. The DNAs were derived from peripheral blood obtained from T-ALL patients before treatment.

Figure 2A:
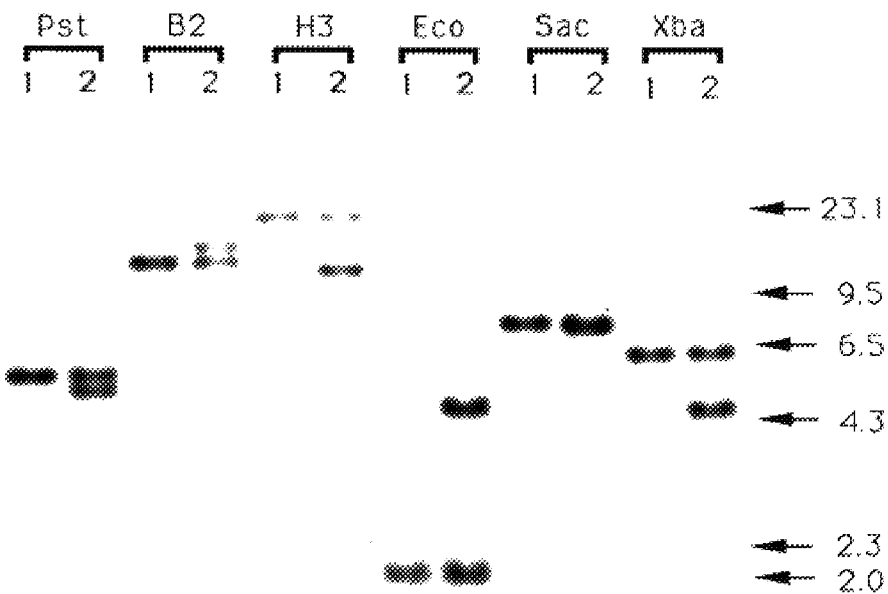
FIGS. 2A–2B shows that tal-1 gene rearrangements in cell lines from unrelated T-ALL patients.

B. The $tal^d$ Rearrangement: A Common Alteration of the tal-1 Gene in about 25% of T-ALL Patients All eight patients with tal-1 gene alterations had rearranged BamHI fragments with identical electrophoretic mobilities (FIG. 1). This phenomenon was investigated further by Southern analyses of T-ALL DNAs digested with six additional restriction endonucleases. FIG. 2A shows the Southern analysis of genomic DNAs digested with any of six different restriction endonucleases and hybridized with the B2EE-2.0 probe. Genomic DNAs were derived from the non-leukemic B cell line RPMI83902 (lanes 1) and the T-ALL cell line RPMI8402 (lanes 2). Thus, FIG. 2A shows the hybridization pattern obtained for DNA from the T-ALL cell line RPMI8402; in each digest the B2EE-2.0 probe detected an equimolar ratio of the normal DNA fragment and a rearranged DNA fragment, indicating that one allele of tal-1 had undergone a structural rearrangement in RPMI8402 cells.

Figure 2B:
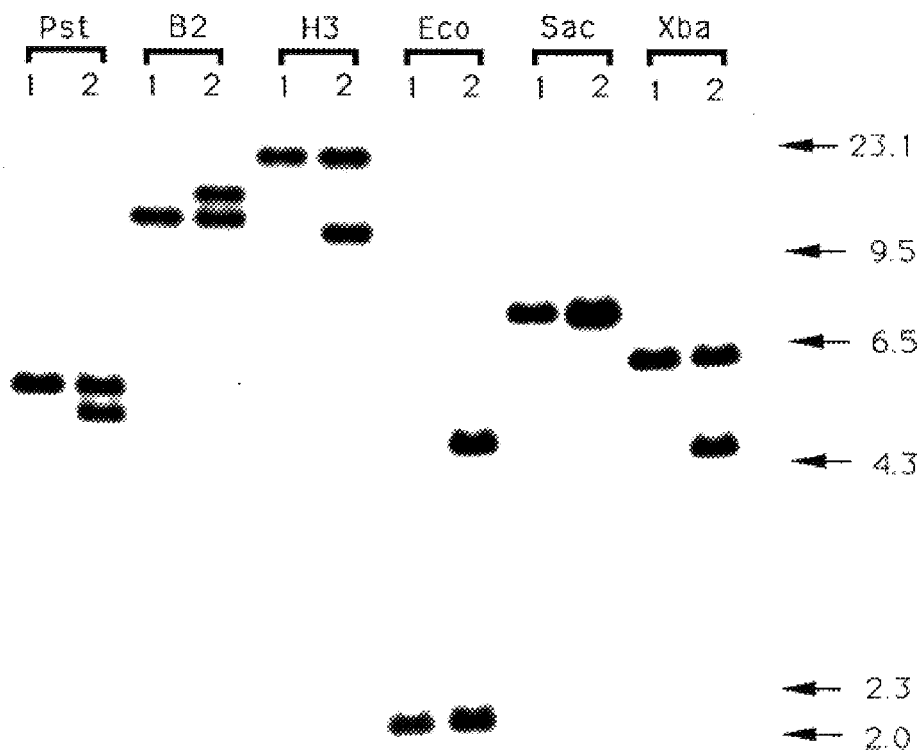

FIG. 2B shows the Southern analysis of DNAs hybridized with the B2EE-2.0 probe. The DNAs of CCRF-CEM, a leukemic cell line derived from an unrelated T-ALL patient are shown by lanes 2; DNA's derived from non-leukemic control cells are shown by lanes 1.

Again, the B2EE-2.0 probe detects DNA rearrangement of one of the two alleles of tal-1. Surprisingly, however, the rearranged DNA fragment in each restriction digest of CCRF-CEM DNA is similar in size to that observed in RPMI8402 DNA, indicating that both cell lines bear an identical rearrangement of the tal-1 locus. Furthermore, an identical pattern of rearranged DNA fragments was obtained upon analysis of each of the other T-ALL samples with tal-1 gene alterations. Therefore, a high proportion of T-ALL patients exhibit a common rearrangement of the tal-1 locus (designated $tal^d$) that, at least at the level of Southern analysis, appears to be the same in each patient.

C. The $tal^d$ Rearrangement is Tumor-Specific

Figure 3:
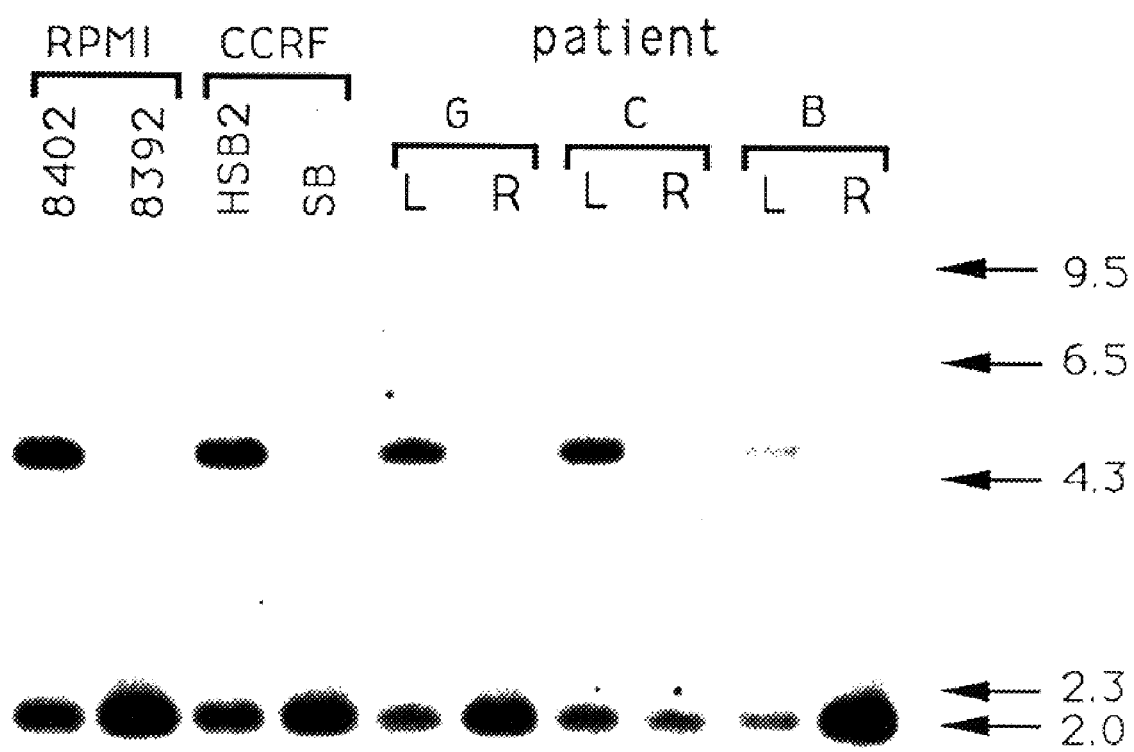
FIG. 3 illustrates that tal$^d$ rearrangements are tumor-specific.

FIG. 3 shows $tal^d$ rearrangements are tumor specific. Southern hybridization analysis of EcoRI-digested DNAs hybridized with the B2EE-2.0 tal-1 probe; $tal^d$ gene rearrangements are seen in DNAs of T-ALL cell lines (RPMI8402 and CCRF-HSB-2) but not non-leukemic B cell lines (RPMI8392 and CCRF-SB, respectively) from the same patients. Similarly, $tal^d$ rearrangements can be detected in DNA from peripheral blood obtained from T-ALL patients before treatment (lanes L) but not after remission induction (lanes R).

Thus, comparative Southern analyses of normal and leukemic cells from the same patient indicate that $tal^d$ rearrangement is tumor-specific. For example, $tal^d$ is apparent in T lymphoblastoid lines from two T-ALL patients (RPMI8402 and CCRF-HSB-2), but not in non-leukemic B cell lines derived from the same patients (RPMI8392 and CCRF-SB, respectively) (Hayata, I. et al. (1975) In Vitro 11, 361–368). Similar results were obtained upon analysis of fresh specimens from T-ALL patients. Three such patients were treated at the Children's Medical Center of Dallas, where blood specimens were obtained before chemotherapy and after complete remission; in each case the leukemic sample bore the $tal^d$ rearrangement and the remission sample did not (FIG. 3). Therefore, $tal^d$ is not a genetic polymorphism of the tal-1 gene, but instead represents an acquired alteration that appears to be restricted to the leukemic cells of T-ALL patients.

D. The $tal^d$ Rearrangement is Generated by Local DNA Recombination

Figure 4A:
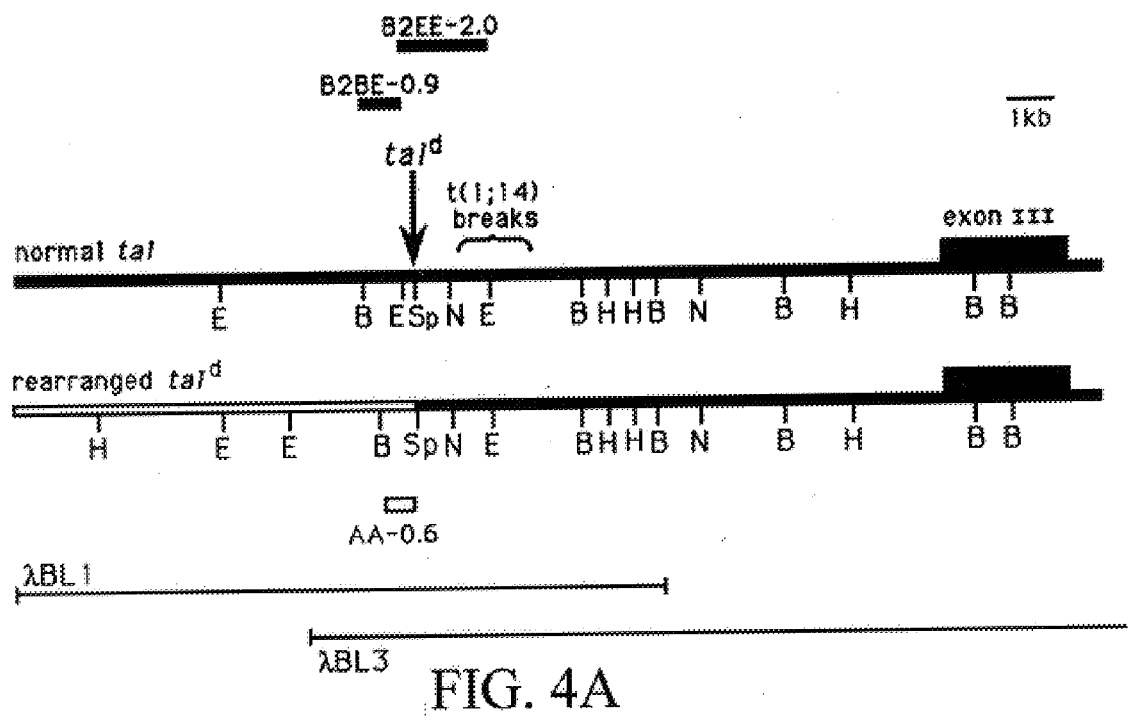
FIGS. 4A–4B shows the structure of the tal$^d$ rearrangement.

To investigate the nature of the $tal^d$ rearrangement, a bacteriophage λ library of genomic DNA from RPMI8402 cells was screened with B2EE-2.0, and several clones with inserts spanning the rearrangement were obtained (e.g., λBL1 and λBL3). In FIG. 4A, it is shown λBL1 and λBL3 clones isolated by screening a library of genomic DNA from the $tal^d$-positive RPMI8402 cell line with probe B2EE-2.0. The restriction map of the rearranged $tal^d$ allele was compiled from those of λBL1 and λBL3, and is compared to that of the normal tal-1 locus. The downstream endpoint of the $tal^d$ deletion is denoted with a large arrow. The B2BE-0.9 and B2EE-2.0 probes are derived from normal tal-1 sequences, and the AA-0.6 probe is derived from novel sequences engendered by the $tal^d$ rearrangement. The major breakpoint region of t(1;14)(p32;q11) is bracketed and the position of the HLH-encoding exon III is indicated. Restriction sites are marked as in FIG. 1A.

Figure 4B:

FIG. 4B depicts a Southern filter identical to that shown in FIG. 2A as being hybridized with the B2BE-0.9 probe. Genomic DNAs in lanes 1 were derived from the non-leukemic B cell line RPMI8392 (lanes 1) and the T-ALL cell line RPMI8402 (lanes 2).

A restriction map encompassing the $tal^d$ rearrangement was compiled by analysis of these clones, and in FIG. 4 this map is compared to that of the normal tal-1 locus. As illustrated, the maps diverge within a 0.25 kb EcoRI-SphI fragment of the normal tal-1 locus, at a position approximately one kb upstream of the t(1;14)(p32;q11) breakpoint region. As a consequence of the rearrangement, novel DNA sequences are juxtaposed with the tal-1 locus (FIG. 4). These sequences are likely to be derived from the same chromosome as tal-1 since RPMI8402 cells do not have karyotypic defects involving the short arm of chromosome 1 (Le Beau, M. M. et al. (1986) Proc. Natl. Acad. Sci. USA 83, 9744–9748). To study this issue, a 0.6 kb DNA fragment (AA-0.6) derived from the novel sequences was used as a probe in Southern hybridizations with DNAs from a panel of human/hamster somatic cell hybrids with randomly segregated human chromosomes (Thompson, L. H. et al. (1987) Som. Cell Mol. Genet. 13, 539–551). The hybridization of AA-0.6 was perfectly concordant with chromosome 1 and randomly associated (18–65% discordancy) with every other human chromosome. The regional localization of AA-0.6 was determined by analysis with a panel of hybrids containing broken derivatives of chromosome 1 (Stallings, R. L. et al. (1988) Am. J. Hum. Genet. 43, 144–151). Since the AA-0.6 probe showed low discordance with short arm markers (17–24%) and high discordance with long arm markers (44–75%), it is likely to be derived from the short arm of chromosome 1. Moreover, the same hybrid panel had been analyzed previously with the B2EE-2.0 probe (Chen, Q. et al. (1990) EMBO J. 9, 415–424), and comparison of the data reveals perfect concordance with AA-0.6. This implies close linkage between the AA-0.6 and B2EE-2.0 sequences. Hence, the $tal^d$ rearrangement represents recombination of local DNA sequences on the short arm of chromosome 1.

Figure 5:
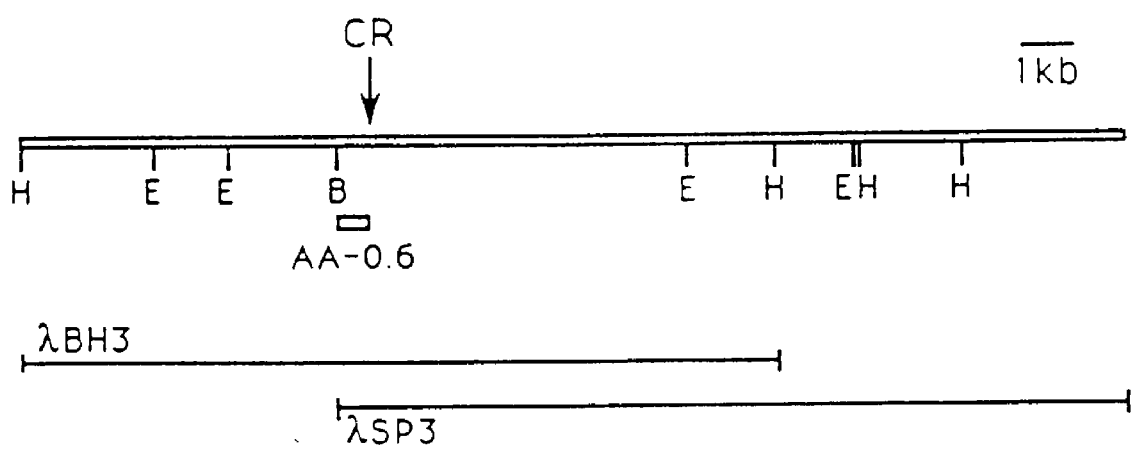
FIG. 5 shows the normal structure of the AA-0.6 locus.

A lambda phage library of SUP-T1 DNA was screened with AA-0.6, and two hybridizing clones were identified (λS3 and λBH3). Restriction analysis of these clones generated a 22 kb map of the normal genomic DNA encompassing AA-0.6 (FIG. 5). FIG. 5 shows the normal structure of AA-0.6 locus. The λBH3 and λSP3 clones were obtained by screening a library of genomic DNA from the $tal^d$-negative cell line SUP-T1 with probe AA-0.6. The restriction map of the unrearranged AA-0.6 locus was compiled from those of λBH3 and λSP3. The upstream endpoint of the $tal^d$ deletion is denoted with an arrow. Restriction sites are marked as in FIG. 1A.

E. The $tal^d$ Rearrangement Represents a DNA Deletion of about 90 kb

The $tal^d$ rearrangement might conceivably arise by any of a number of distinct processes, including local DNA inversion, duplication, insertion or deletion. To evaluate these possibilities, both normal and leukemic DNAs were hybridized with B2BE-0.9, a probe located immediately upstream of B2EE-2.0 in normal DNA, but on the opposite flank of the rearrangement site (see FIG. 4A). If $tal^d$ rearrangement occurs without loss of genetic material, then Southern analyses with B2BE-0.9 should reveal rearranged DNA fragments upon digestion of RPMI8402 DNA with restriction enzymes that recognize sites flanking both B2BE-0.9 and B2EE-2.0 (e.g., BamHI, HindIII, BglII, PstI). Nevertheless, as shown in FIG. 4B, only normal DNA fragments are detected with B2BE-0.9. Hence, one allele of B2BE-0.9 has been lost from the genome of RPMI8402. B2BE-0.9 exhibits the same pattern of hybridization with genomic DNA from each of the other T-ALL samples that bear $tal^d$. These results are consistent with a model in which $tal^d$ is generated by local DNA deletion, with concomitant loss of sequences between the two recombining elements (represented by AA-0.6 and B2EE-2.0).

Figure 6A:
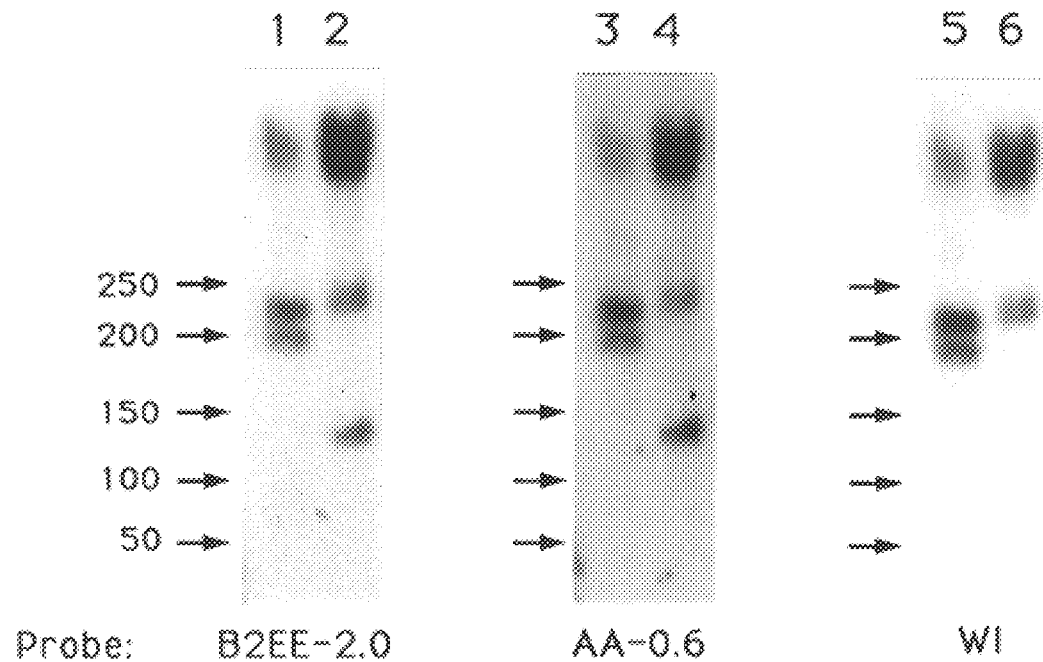
FIGS. 6A–6B illustrates the tal$^d$ rearrangement generates a 90 kilobasepair deletion.
Figure 6B:
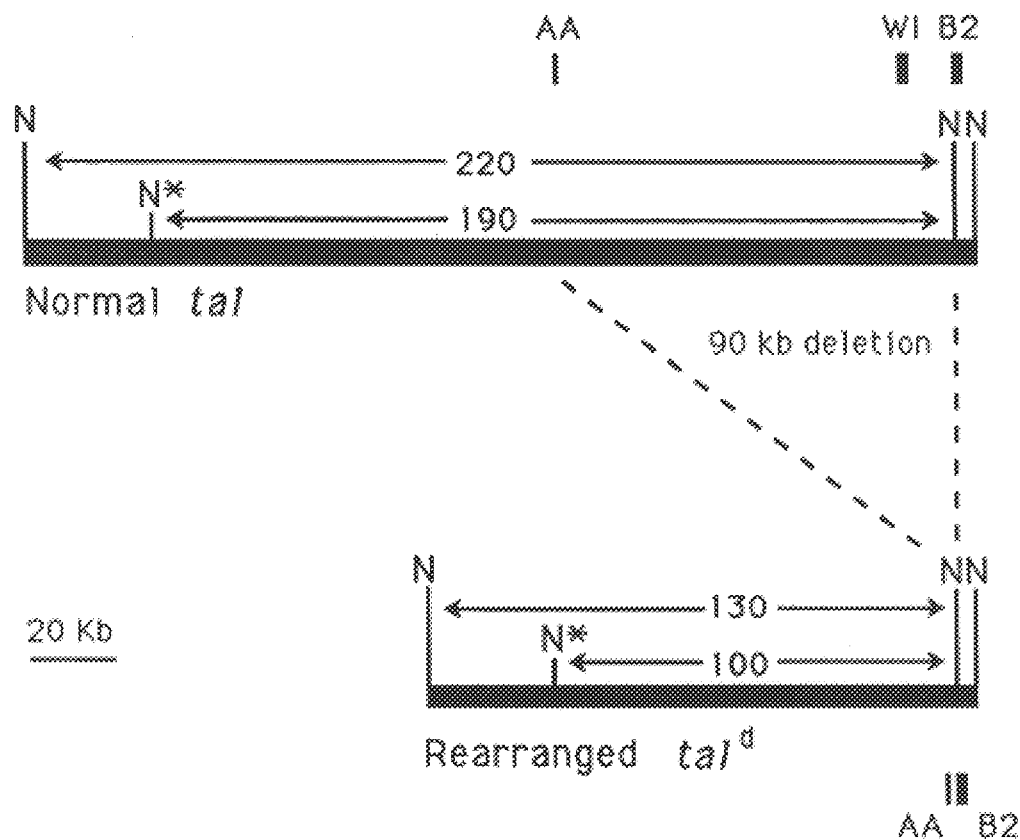

Although AA-0.6 and B2EE-2.0 originate from the same region of chromosome 1, the restriction maps of normal genomic DNA around these markers do not overlap. Indeed, direct comparison of these maps indicates that AA-0.6 and B2EE-2.0 are separated by at least 35 kb (FIGS. 1A and 5). Consequently, if $tal^d$ is generated by simple deletion, then the segment of DNA deleted is likely to be substantial. To evaluate the linkage between AA-0.6 and B2EE-2.0, NotI-digested DNAs from RPMI8392 and RPMI8402 cells were fractionated by transverse alternating field electrophoresis, and analyzed by Southern hybridization (FIG. 6A). FIG. 6A shows that NotI-digested genomic DNAs from the non-leukemic B cell line RPMI8392 (lanes 1, 3, and 5) and the T-ALL cell line RPMI8402 (lanes 2, 4, and 6) were fractionated by pulsed-field gel electrophoresis and transferred to a membrane filter. The filter was hybridized, stripped of radioactivity and rehybridized successively with probes B2EE-2.0 (FIG. 4A), AA-0.6 (FIG. 4A), and WI (FIG. 6B). Size markers are concatamers of λDNA spaced at about 50 kb intervals.

FIG. 6B shows the NotI restriction map of the normal and rearranged alleles of tal-1. The positions of the AA-0.6 (AA), WI, and B2EE-2.0 (B2) probes are indicated. The WI probe represents sequences located 12 kb upstream of B2EE-2.0 in the normal tal-1 allele. The sizes of NotI restriction fragments that co-hybridize with AA-0.6 and B2EE-2.0 are indicated in kb. The asterisk denotes the NotI site that exhibits variable resistance to NotI digestion.

Interestingly, the AA-0.6 and B2EE-2.0 probes co-hybridized with NotI fragments of 220 and 190 kb in DNA from RPMI8392 (FIG. 6A, lanes 1 and 3), a B-lymphoblastoid line that does not bear the $tal^d$ rearrangement. Southern analyses of NotI-digested DNAs from other cell lines without $tal^d$ exhibit a variable pattern in which the AA-0.6 and B2EE-2.0 probes co-hybridize with either two fragments of 220 and 190 kb or a single fragment of 220 kb. Therefore, in normal DNA the AA-0.6 and B2EE-2.0 markers reside within a 190 kb NotI fragment; the 220 kb species is likely to arise in certain cell lines as a consequence of partial cytosine methylation at one of the flanking NotI sites. Restriction analysis of cloned DNA encompassing the tal-1 locus identified several NotI sites, one of which lies within B2EE-2.0 (FIG. 1A). Hence, the B2EE-2.0 probe overlaps neighboring NotI fragments of 190 kb and 5.3 kb in normal DNA. Tal-1 gene probes located downstream of the 5.3 kb NotI fragment hybridize to a NotI fragment of greater than 500 kb; therefore, the 220 kb species detected with B2EE-2.0 is likely to be generated due to partial methylation of the upstream (rather than the downstream) NotI site of the 190 kb fragment, as shown schematically in FIG. 6B.

The relative position of AA-0.6 within the 190 kb fragment can be deduced by Southern analysis of NotI-digested DNA from cells bearing $tal^d$. For example, in RPMI8402 cells the $tal^d$ rearrangement generates a 130 kb NotI fragment that co-hybridizes with the AA-0.6 and B2EE-2.0 probes (FIG. 6A, lanes 2 and 4). In other $tal^d$-positive cell lines, these probes co-hybridize with either a single rearranged 130 kb fragment (e.g., CCRF-CEM) or with two rearranged fragments of 130 and 100 kb (e.g., CCRF-HSB-2). Again, these patterns are compatible with variable methylation at the distal NotI site of the smaller fragment (FIG. 6B). AA-0.6 must be located near one end of this fragment since, as a result of $tal^d$ rearrangement, AA-0.6 is closely juxtaposed with B2EE-2.0 sequences that contain a NotI recognition site. As depicted schematically in FIG. 6B, this in turn localizes AA-0.6 to a position approximately 90 kb upstream of B2EE-2.0 in normal genomic DNA. It is noteworthy that tal-1 DNA probes located between AA-0.6 and B2EE-2.0 (e.g., W1; FIG. 6B) hybridize with the normal 220/190 kb NotI fragment(s) but not with the rearranged 130/100 kb species (FIG. 6A, lanes 5 and 6). This provides further support for a deletional model in which $tal^d$ arises by site-specific recombination between AA-0.6 and B2EE-2.0, accompanied by loss of the 90 kb of intervening sequence.

F. The $tal^d$ Rearrangement is Site-Specific

In view of its substantial size, it is surprising that the $tal^d$ deletion is indistinguishable—at least at the level of Southern analysis—in different T-ALL patients. As shown in FIG. 4, the deletion junction from RPMI8402 cells can be localized to a 0.7 kb BamHI-SphI fragment, the sequence of which is presented in FIG. 7, which shows the nucleotide sequence encompassing the $tal^d$ rearrangement of RPMI8402. The sequence includes the 0.7 kb BamHI-SphI fragment of the $tal^d$ allele of RPMI8402 cells. The rearrangement site was determined by comparative analysis of normal and rearranged tal-1 sequences (see FIG. 8). The positions of synthetic oligonucleotide primers are indicated; the oligonucleotide C sequence is as shown, whereas the oligonucleotide D sequence is the reverse complement of that shown.

The nucleotide sequences of corresponding germline DNA in the vicinity of AA-0.6 and B2EE-2.0 were determined. In FIG. 8, these sequences are aligned so as to illustrate the deletion junction. Interestingly, the RPMI8402 junction contains a stretch of nine nucleotides which are not derived from germline sequences in the region of either AA-0.6 or B2EE-2.0.

Deletion junctions of $tal^d$ were isolated from additional patients by the polymerase chain reaction. Hence, oligonucleotide primers that flank the RPMI8402 junction (i.e., oligos C and D; FIG. 8) were used to amplify genomic DNAs from various sources, including leukemic cells from twenty-one T-ALL patients with $tal^d$. FIG. 8 shows the deletion junction of $tal^d$ from RPMI8402 cells. The $tal^d$ deletion junction of RPMI8402 (B) is identified by comparison with germline sequences of the AA-0.6 region (A) and the B2EE-2.0 region (C). The nine nucleotide residues at the junction (in lowercase letters) are not derived from germline sequences of AA-0.6 or B2EE-2.0. Heptamer sequences of the putative recombination signals are marked with asterisks.

In this manner, a discrete amplification product of approximately 220 basepairs was generated from each of the $tal^d$-positive DNAs, but not from genomic DNAs without $tal^d$. Nucleotide sequence analyses confirmed that the amplified product from each patient represents the deletion junction of $tal^d$; thus, as shown in FIG. 9, each product is comprised of AA-0.6 sequences juxtaposed with B2EE-2.0 sequences in a fashion similar to that of the RPMI8402 junction. FIG. 9 depicts $tal^d$ deletion junctions as resembling the coding joints of assembled immunoglobulin genes. The $tal^d$ junctions of three additional $tal^d$-positive cell lines and 18 $tal^d$-positive primary T-ALL specimens were isolated by PCR amplification using oligonucleotides C and D (FIG. 7). The $tal^d$ junctions are aligned with germline sequences from AA-0.6 and B2EE-2.0. Heptamer sequences of the putative recombination signals within AA-0.6 and B2EE-2.0 are marked with asterisks, and the proposed sites of recombination are denoted with arrows. Junctional nucleotides in lowercase letters are not derived from the germline sequences of AA-0.6 or B2EE-2.0. The underlined thymidine residues at the AA-0.6 junctions of CCRF-HSB-2, MOLT16, patients 60, 80, and 83 are proposed to be P nucleotides (Lafaille, J. J. et al. (1990) Cell 59, 859–870).

Nevertheless, the deletion junction from each patient is unique due to sequence variation at the recombination site (FIG. 9). As discussed above, the junctional diversity generated by the $tal^d$ rearrangement is reminiscent of that engendered during site-specific rearrangement of the immunoglobulin and T cell receptor genes.

Fluorescent In Situ Chromosome Hybridization

Leukemic cells that harbor the tal-1 gene deletion can also be readily identified by fluorescent in situ chromosome hybridization (FISH). Within a given leukemic cell, the tal-1 deletion only involves one of the two homologs of chromosome 1. In these cells, DNA probes that recognize tal-1 sequences located within the 90 kb deletion region (hereafter referred to as "deletion probes") will hybridize to one homolog (i.e., the normal homolog) of chromosome 1, whereas DNA probes that recognize other sequences on chromosome 1 (referred to as "control probes") will hybridize to both homologs. The hybridization patterns of the deletion probe and the control probe can be distinguished by a two-color FISH analysis in which each probe is marked with a distinct fluorochrome such as Texas red or fluorescein isothiocyanate (FITC). A typical general protocol for detection of the tal-1 deletion by FISH is as follows:

The deletion probe (green, e.g., λSU25, see below) is nick-translated (Bethesda Research Laboratories Nick-Translation System) with digoxigenin-11-dUPT (deoxyuridine 5'-triphosphate) (Boehringer Mannheim Biochemicals) and the control probe (red, e.g., L-myc genomic DNA) is similarly nick-translated with biotin-11-dUTP (Enzo Diagnostic). These probes are then hybridized to either interphase nuclei or metaphase spreads of the cells to be tested under conditions essentially described by Tkachuk et al. (Tkachuk, D. C. et al. (1990) Science 250, 559–562). The digoxigenin-labelled deletion probe is then detected by incubation with sheep-antibody to digoxigenin followed by FITC-conjugated rabbit-antibody to sheep-antibody. The biotin-labelled control probe is detected by incubation with Texas red-avidin. The hybridization signals of both probes are then visualized simultaneously with a fluorescent microscope equipped with a double band-pass filter set. Two-color FISH with the deletion (green) and control (red) probes should result in two green and two red hybridization signals in the nuclei of normal cells. In contrast, a single green and two red hybridization signals should be observed in leukemic cells that harbor the tumor-specific tal-1 gene deletion.

DNA from the phage clones λSU25 and λWI11 can be used as "deletion probes". λSU25 and λWI11 each contain a genomic DNA fragment (13.7 and 15.6 kb, respectively) from the tal-1 gene deletion region that has been inserted into the λ2001 phage vector. Virtually any other sequence derived from chromosome 1 can serve as the "control probe". However, to ensure that the fluorescence signals from the deletion and control probes can be resolved, it may be preferable to use a control probe that is not closely linked to the tal-1 locus at 1p32–34.

Specifically, detection of the tal-1 gene deletion by FISH can be carried out as follows:

Test cells are to be hybridized by a published procedure (Pinkel, D. et al. (1988) Proc. Natl. Acad. Sci. U.S.A. 85, 9138). Cells are thermally denatured at 72° C. for about 5 min, dehydrated in an ethanol series, air-dried, and then can be placed at 37° C. A hybridization mixture (10 μl) containing each probe (2 ng/μl), 50% formamide/2×standard saline citrate (SSC), 10% dextran sulfate, and human genomic DNA (1 mg/ml, sonicated to 200 to 600 bp) is then heated to about 70° C. for about 5 min, incubated for about 30 min at 37° C., placed on the warmed slides, covered with a 20 mm by 20 mm cover slip, sealed with rubber cement, and incubated overnight at 37° C. Slides are washed three times in 50% formamide/2×SSC for about 20 min each at 42° C., twice in 2×SSC at 42° C. for about 20 min each, and rinsed at room temperature in 4×SSC. All subsequent steps can be performed at room temperature. Slides are blocked in 100 μl of 4×SSC/1% bovine serum albumin (BSA) for about 5 min under a cover slip. The biotinylated control probe is detected by applying 100 μl of Texas red-avidin (Vector Laboratories Inc., 2 μg/ml in 4×SSC/1% BSA) for about 45 min. The slides are washed twice for 5 min in 4×SSC/1% Triton X-100 (Sigma). The signal is amplified by applying biotinylated goat antibody to avidin {Vector Laboratories Inc., 5 μg/ml in PNM [0.1M NaH$_2$PO$_4$/0.1M Na$_2$HPO$_4$, pH 8 (PN) containing 5% nonfat dry milk and 0.02% sodium azide and centrifuged to remove solids]}, washed twice in PN for about 5 min, followed by another layer of Texas red-avidin in PNM. The digoxigenin-labeled deletion probe is detected by incubation with sheep antibody to digoxigenin (Boehringer Mannheim Biochemicals, Indianapolis, Ind.; 15.4 μg/ml in PNM) for about 30 min, washed twice in PN for about 5 min, followed by a rabbit-antibody to sheep conjugated with FITC (Organon Teknika-Cappel, 1:50 in PNM). After washing twice for about 5 min in PN, the signal can be amplified by applying a sheep antibody to rabbit immunoglobulin G (IgG) conjugated to FITC (Organon Teknika-Cappel, 1:50 in PNM). The slides are then rinsed in PN. Slides are mounted in 10 μl of fluorescence antifade solution [Johnson, G. D. and Nogueria, J. G. (1981) J. Immunol. Methods 43, 349) containing 4',6-amidino-2-phenylindole (DAPI) at 1 μg/ml as a counterstain. The slides can be examined with an FITC/Texas red double-band pass filter set (Omega Optical) on a Zeiss Axioskop.

Thus, this invention shows that tal-1 locus alteration on chromosome 1 represents the best genetic marker available for the diagnosis and prognosis of T-ALL. Tal-1 locus alteration on chromosome 1 is common among T-ALL patients, observable in about 25% of patients. It is specific to T-ALL patients, and not observed in other types of primary leukemia, and is very easy to detect. Genetic markers of T-ALL are currently of two types: (1) chromosome abnormalities detected by karyotype analysis; and (2) T cell receptor gene rearrangements detected by Southern hybridization analysis or the polymerase chain reaction. Tal-1 locus alteration on chromosome 1 is a superior marker for T-ALL because it is easier to detect than chromosome abnormalities and because, unlike T cell receptor gene rearrangements, it is specific to the leukemic cells of T-ALL patients. This invention thus is useful for the diagnosis and prognosis of T-ALL. It can also be used to track minimal levels of residual leukemic cells in patients during treatment and during remission.

Publications cited throughout here show what is known in the art. These publications are hereby incorporated by reference.

While the present invention has been particularly described in terms of specific embodiments thereof, it will be understood in view of the present disclosure that numerous variations upon the invention are now enabled to those skilled in the art, which variations yet reside within the scope of the present invention. Accordingly, the invention is to be broadly construed, and limited only by the scope and spirit of the claims now appended hereto.

I claim:

1. A method for detecting presence of hematopoietic tumors in a patient, said method comprising:
    combining for hybridization (1) a deletion probe, having a first fluorochrome, said deletion probe substantially matching an altered human chromosome 1 having a tal-1 deletion indicative of presence of said hematopoietic tumors and said deletion probe being a nucleic acid sequence capable of hybridizing with the altered human chromosome 1 having said deletion; (2) a control probe, having a second fluorochrome, said control probe substantially matching both a normal and the tal-1 altered human chromosome 1 and said control probe being a nucleic acid sequence capable of hybridizing with the normal human chromosome 1; and (3) cells suspected of containing a deletion at the tal-1 locus on chromosome 1 from said patient;

hybridizing in situ the cells and said deletion probe and said control probe; and analyzing the hybridization patterns of the cells and said deletion probe and/or said control probe for an indication of the presence of a tal-1 deletion, indicating the presence of said hematopoietic tumors in said patient.

2. A method of claim 1 wherein said deletion occurs at a genetic locus involved in leukemogenesis.

3. A method of claim 1 wherein said deletion is of about 90 kilobasepair disrupting the upstream sequence of the T-cell acute leukemia gene, tal-1.

4. A deletion probe comprising:
    a nucleic acid sequence derived from phage clone λSU25 from a tal-1 gene deletion region that has been inserted in λ2001 phage vector, said nucleic acid sequence substantially matching with a normal human chromosome 1 and capable of hybridizing with said normal human chromosome 1, but not substantially matching with a human chromosome 1 having a deletion indicative of presence of hematopoietic tumor.

5. The deletion probe of claim 4 wherein said human chromosome 1 comprises a 90 kilobasepair deletion involving tal-1 gene that is associated with T-cell acute lymphoblastic leukemia.

6. A method for detecting T-cell acute lymphoblastic leukemia in a human, said method comprising the step of:
    detecting, by fluorescent in situ chromosome hybridization, a deletion in tal-1 locus on chromosome 1 in cells isolated from said human, said deletion being associated with the existence of T-cell acute lymphoblastic leukemia.

7. The method of claim 6, further comprising the step of removing a tissue from said human as a source of said cells.

8. The method of claim 6, wherein said deletion is a deletion of about 90 kilobasepair disrupting the upstream sequence of the T-cell acute leukemia gene tal-1.

9. A method for detecting T-cell acute lymphoblastic leukemia in a patient, said method comprising the steps of:
    combining sufficient for in situ hybridization: (1) a deletion probe, having a first fluorochrome, said deletion probe substantially matching an altered human chromosome 1 and said deletion probe being a nucleic acid sequence capable of hybridizing with said altered human chromosome 1; (2) a control probe, having a second fluorochrome, said control probe substantially matching both a normal and the altered human chromosome 1 and said control probe being a nucleic acid sequence capable of hybridizing with said normal human chromosome 1; and (3) cells from said patient suspected of containing a deletion in the tal-1 locus on chromosome 1; and detecting any hybridization of said deletion probe and said control probe with said cells as an indication of the presence of said T-cell acute lymphoblastic leukemia in said patient.

* * * * *

UNITED STATES PATENT AND TRADEMARK OFFICE
CERTIFICATE OF CORRECTION

PATENT NO : 5,840,492
DATED : November 24, 1998
INVENTOR(S) : Richard J. Baer

It is certified that error appears in the above-identified patent and that said Letters Patent are hereby corrected as shown below:

On the title page item

[54] TITLE         Replace "METHOD"
                   With --METHODS--

[57] ABSTRACT      Replace "in situ"
                   With --in in situ--

Column 15, line 23 Replace "[Johnson"
                   With --(Johnson--

Signed and Sealed this

Twenty-fourth Day of April, 2001

NICHOLAS P. GODICI

Attest:

Attesting Officer    Acting Director of the United States Patent and Trademark Office